United States Patent
Blevis

(10) Patent No.: US 9,658,345 B2
(45) Date of Patent: May 23, 2017

(54) RADIATION DETECTOR AND DETECTION METHOD HAVING REDUCED POLARIZATION

(71) Applicant: KONINKLIJKE PHILIPS N.V., Eindhoven (NL)

(72) Inventor: Ira Micah Blevis, Zichron Yaakov (IL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 15/031,776

(22) PCT Filed: Oct. 27, 2014

(86) PCT No.: PCT/IB2014/065625
§ 371 (c)(1),
(2) Date: Apr. 25, 2016

(87) PCT Pub. No.: WO2015/063665
PCT Pub. Date: May 7, 2015

(65) Prior Publication Data
US 2016/0245932 A1    Aug. 25, 2016

Related U.S. Application Data

(60) Provisional application No. 61/898,855, filed on Nov. 1, 2013.

(51) Int. Cl.
*A61B 6/03* (2006.01)
*G01T 1/24* (2006.01)

(52) U.S. Cl.
CPC ............... *G01T 1/24* (2013.01); *A61B 6/037* (2013.01)

(58) Field of Classification Search
CPC ................................ A61B 6/037; G01T 1/24
See application file for complete search history.

(56) References Cited

U.S. PATENT DOCUMENTS

| | | | |
|---|---|---|---|
| 5,905,264 A | 5/1999 | Shahar | |
| 6,175,120 B1 | 1/2001 | McGregor | |
| 7,145,721 B2 * | 12/2006 | Banish | G02B 1/11 216/24 |
| 7,223,982 B1 | 5/2007 | Chen | |
| 8,084,746 B2 | 12/2011 | Kim | |
| 8,426,826 B2 | 4/2013 | Proksa | |

(Continued)

FOREIGN PATENT DOCUMENTS

| | | | |
|---|---|---|---|
| DE | 102011083532 | 2/2013 | |
| DE | 102011083532 A1 * | 2/2013 | G01T 1/241 |

(Continued)

*Primary Examiner* — Mark R Gaworecki

(57) ABSTRACT

A radiation-sensitive detector array (100) including a first side (120), a second side (110) in opposed relation to the first side, and a detector substrate (130) positioned between the first and second sides is presented. The first side is constructed as a non-planar or uneven shape. The first side is a cathode and the second side is an anode. The cathode may be a field emission cathode (FEC) and the detector substrate may be a Cadmium Zinc Telluride (CZT) detector substrate. The non-planar or uneven shape may be a series of equally spaced apart protrusions, each of the protrusions being a pyramidal construction including a peak, the peak adapted and dimensioned to cause electric field lines to focus or converge thereon.

20 Claims, 5 Drawing Sheets

(56) References Cited

U.S. PATENT DOCUMENTS

2002/0135869 A1* 9/2002 Banish .................... G02B 1/11
　　　　　　　　　　　　　　　　　　　359/350
2008/0164418 A1　7/2008 Shahar

FOREIGN PATENT DOCUMENTS

EP　　　　2144271　　1/2010
WO　　2006/083109　　8/2006

* cited by examiner

0
RADIATION DETECTOR AND DETECTION METHOD HAVING REDUCED POLARIZATION

CROSS REFERENCE TO RELATED APPLICATIONS

This application is the U.S. National Phase application under 35 U.S.C. §371 of International Application No. PCT/IB2014/065625, filed Oct. 27, 2014, published as WO 2015/063665 on May 7, 2015, which claims the benefit of U.S. Provisional Patent Application No. 61/898,855 filed Nov. 1, 2013. These applications are hereby incorporated by reference herein.

BACKGROUND

Technical Field

The present disclosure relates to radiation detectors, such as radiation detectors used in computed tomography (CT). More particularly, the present disclosure relates to a direct conversion radiation detector and detection method utilizing a cathode with an uneven surface for focusing field lines of an electric field at particular locations along the uneven surface of the cathode to reduce polarization.

Description of Related Art

A medical imaging system may include an array of indirect conversion (scintillator/photosensor) detectors such as a gadolinium oxysulfide (GOS) detectors or direct conversation detectors such as Cadmium Zinc Telluride (CZT) detectors. Direct conversion detectors directly convert detected radiation to electrical signals such as an electrical current.

An example direct conversion detector includes a CZT radiation sensitive semiconductor substrate with a first side that receives radiation and a second opposing side with electrical contacts for transferring corresponding electrical signal. The radiation sensitive semiconductor substrate may be partitioned into a plurality of rows of detector elements and a plurality of columns of detector elements to form a two dimensional array of detector elements. Each detector element is associated with a corresponding electrical contact for transferring the corresponding electrical signal to a readout substrate, which in turn includes electrical contacts for transferring the electrical signal off of the detector.

Radiation detectors, e.g., detectors capable of detecting X-rays and/or gamma rays, have been developed over the years for a variety of applications, e.g., medical imaging and detection, non-destructive testing and security inspection. Some early detectors included a collimator, a scintillation crystal and a plurality of photomultiplier tubes (PMTS). To overcome some shortcomings associated with PMT detectors, direct conversion detectors have been developed. Direct conversion detectors are capable of operating in photon counting mode or current mode.

Direct conversion radiation detectors, e.g., radiation detectors using Cadmium Zinc Telluride (CZT) or some other direct conversion material, have been developed for a variety of applications. Research on CZT has been primarily devoted to photon counting applications. Typically, these photon counting applications use gamma sources with flux rates that range from 1 photon per second up to at least $10^6$ photons per second. These high flux rate applications may use Bremstrahlung sources, such as conventional X-ray tubes. These sources typically supply much higher fluence than gamma sources, even at their lowest range of operation, which is in the range of $10^6$ photons per second to up to $10^9$ photons per second. What's more is that X-ray tubes are polychromatic sources that output a wide spectrum of energies which has a significant effect on how these photons interact with the detection material.

Direct conversion radiation detectors traditionally have been plagued by polarization effects for high count rates in photon counting mode and non-planar response in current mode. The cause of the polarization may be the result of one of the carriers, either electron or hole, having a significantly lower mobility($\mu$)-lifetime($\tau$) product ($\mu\tau_e$—mu-tau electrons; $\mu\tau_j$—mu-tau holes) than the other carrier.

Therefore, there is an increasing need to develop radiation-sensitive detection filters that minimize polarization effects.

SUMMARY

Aspects of the present application address the above-referenced matters and others.

In accordance with aspects of the present disclosure, a radiation-sensitive detector array is presented. The radiation-sensitive detector array includes a first side, a second side in opposed relation to the first side, and a detector substrate positioned between the first and second sides. The first side is constructed as a non-planar shape.

According to a further aspect of the disclosure, the non-planar shape is a series of equally spaced apart protrusions (such as, for example, lenticular, saw-tooth, sinusoidal, etc.). The non-planar shape extends towards the first side. In one exemplary embodiment, each of the protrusions is of a pyramidal construction. Each of the pyramidal constructions includes a peak, the peak adapted and dimensioned to cause electric field lines to converge thereon. In another exemplary embodiment, each of the protrusions is of rounded construction.

According to a further aspect of the disclosure, the electric field lines are at least ten times stronger at the peaks of each of the pyramidal constructions than at other regions of the detector substrate.

According to another aspect of the disclosure, the FEC is constructed by milling the detector substrate. Moreover, polishing may be performed after milling.

According to yet another aspect of the present disclosure, the detector array is a direct conversion detector array.

According to a further aspect of the present disclosure, the detector array is a part of a single photon emission computed tomography (CT) scanner.

According to another aspect of the present disclosure, the first side is a cathode and the second side is an anode. The cathode may be a field emission cathode (FEC) and the detector substrate may be a Cadmium Zinc Telluride (CZT) detector substrate.

According to yet another aspect of the disclosure, the first and second sides detect incident radiation, whereas the detector substrate produces a signal indicative of the detected radiation.

According to yet a further aspect of the disclosure, a method for concentrating electric field lines in a radiation-sensitive detector array is presented. The method includes the steps of positioning a first side in opposed relation to a second side, positioning a detector substrate between the first and second sides, and constructing the first side as a non-planar shape.

Further scope of applicability of the present disclosure will become apparent from the detailed description given hereinafter. However, it should be understood that the detailed description and specific examples, while indicating preferred embodiments of the present disclosure, are given by way of illustration only, since various changes and modifications within the spirit and scope of the present disclosure will become apparent to those skilled in the art from this detailed description.

BRIEF DESCRIPTION OF THE DRAWINGS

The aspects of the present disclosure may be better understood with reference to the following figures. The components in the figures are not necessarily to scale, emphasis instead being placed upon clearly illustrating the principles of the disclosure. Moreover, in the figures, like reference numerals designate corresponding parts throughout the several views.

In the figures.

DETAILED DESCRIPTION

Although the present disclosure will be described in terms of a specific embodiment, it will be readily apparent to those skilled in this art that various modifications, rearrangements and substitutions may be made without departing from the spirit of the present disclosure. The scope of the present disclosure is defined by the claims appended hereto.

Computed tomography (CT) is the science of creating two-dimensional cross-sectional images from projection images taken at different angles. CT utilizes a mathematical technique called reconstruction to achieve such task. Thus, CT is a mathematical process. A CT image is the result of breaking apart a three-dimensional structure and mathematically putting it back together and displaying it as a two-dimensional image on a display screen. The goal of the CT system is to accurately reproduce the internal structures of the body as two-dimensional cross-sectional images. Collecting many projections of an object and filtration of the x-ray beams are important factors in CT image formation. The present disclosure relates to an x-ray device, particularly in the form of a Computed Tomography (CT) scanner, which includes at least a radiation source and a beam filter. The radiation source may include a radiation-sensitive detector array, described below.

Figure 1:
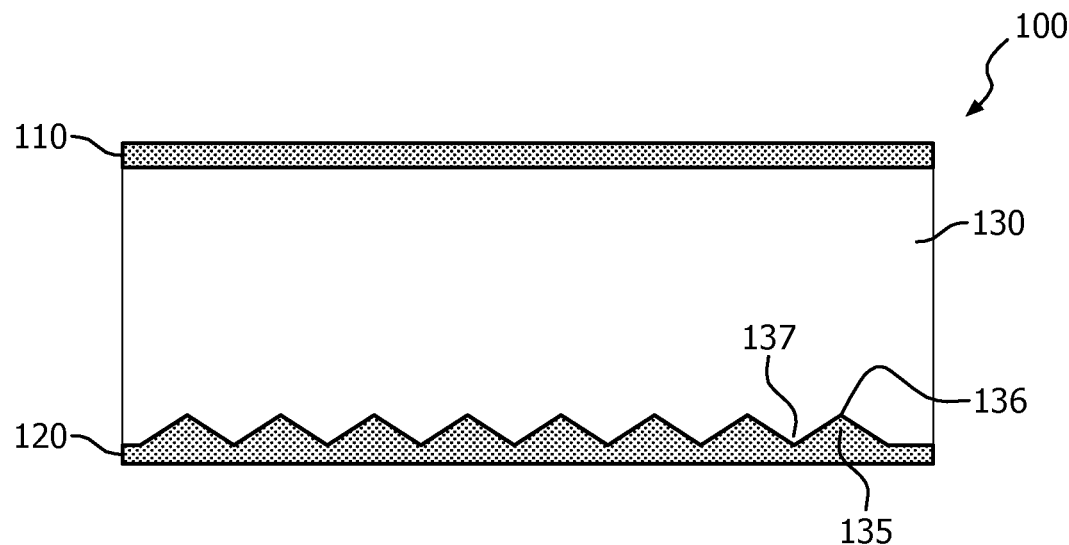
FIG. 1 illustrates a radiation-sensitive detector array having a field emission cathode (FEC), according to the present disclosure.

Referring to FIG. 1, a radiation-sensitive detector array having a field emission cathode (FEC), according to the present disclosure is presented.

The radiation-sensitive detector array 100 includes a first side 120 and a second side 110. The first side 120 is a cathode, whereas the second side 110 is an anode. The cathode 120 may be a field emission cathode (FEC). The second side 110 is in opposed relation to the first side 120. A detector substrate 130 is positioned between the first side 120 and the second side 110. The detector substrate 130 may be a Cadmium Zinc Telluride (CZT) detector substrate.

Figure 2:
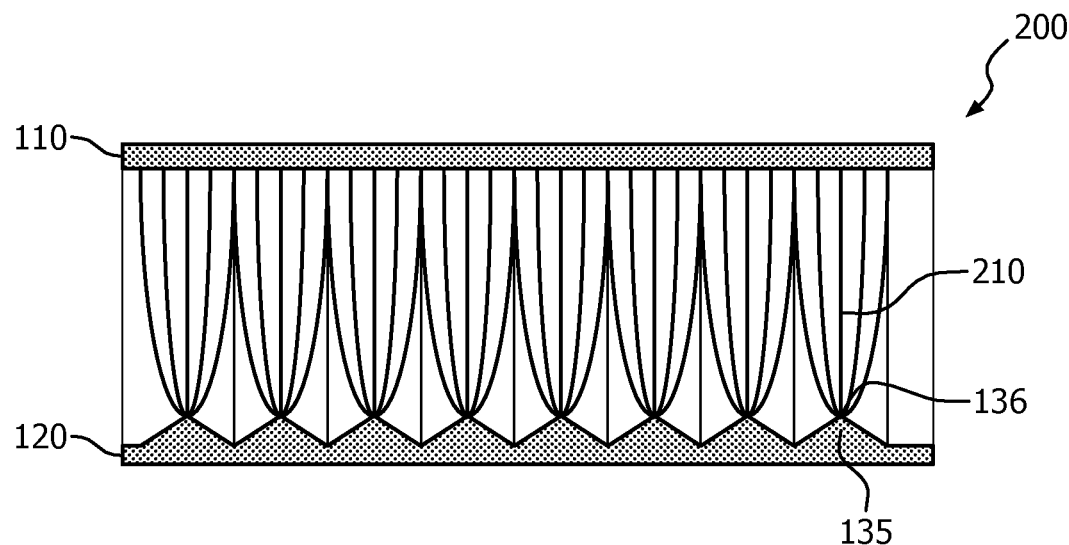
FIG. 2 illustrates electric field lines generated upon application of current to the radiation-sensitive detector array of FIG. 1, according to the present disclosure.

The first side 120 is constructed as a non-planar or uneven shape. The non-planar or uneven shape may be an irregular shape. The non-planar shape may be a series of equally spaced apart protrusions 135, such as, for example, lenticular, saw-tooth, sinusoidal, etc. Each of the protrusions 135 may be a pyramidal shape or construction or configuration, where each pyramidal shape 135 includes a peak 136, the peak 136 adapted and dimensioned to cause electric filed lines to converge thereon, as shown in FIG. 2. As a result of the pyramid construction of the protrusions 135, a valley 137 is presented therebetween each protrusion 135. The valley 137 may also be referred to as an intrusion.

One skilled in the art may contemplate any type of irregular shape for the protrusions 135 having sharp or rounded edges/tips. One skilled in the art may contemplate the protrusions 135 being spaced apart at random intervals, thus being non-equally spaced apart.

Referring to FIG. 2, electric field lines generated upon application of current to the radiation-sensitive detector array of FIG. 1, according to the present disclosure are presented.

In FIG. 2, a current is applied to the radiation-sensitive detector array 100 of FIG. 1, such that the first and second sides 110, 120 detect incident radiation, whereas the CZT detector substrate 130 produces a signal indicative of the detected radiation. As shown in the configuration 200 of FIG. 2, electric field lines 210 extend the vertical length of the radiation-sensitive detector array 100 between the first and second sides 110, 120.

As illustrated in configuration 200, the electric field lines 210 converge or focus on the peaks 136 of the protrusions 135, thus minimizing polarization effects of the radiation-sensitive detector array 100. Thus, the electric field lines 210 do not converge on the first side 110, since the electric field lines 210 are spaced apart from each other, whereas the electric field lines 210 tend to focus or converge on the second side 120, as a result of the protrusions 135. Thus, the produced curvature of the points/peaks/tips of the cathode 120 cause focusing or converging of the electric field lines 210. The electric field lines 210 are at least ten times stronger at the peaks 136 of each of the pyramidal constructions 135 than at other regions of the CZT detector substrate 130. Thus, the detection method described utilizes a cathode 120 with an uneven surface for focusing electric field lines 210 of an electric field at particular locations (e.g., peaks 136) along the uneven surface of the cathode 120 to reduce polarization.

Figure 3:
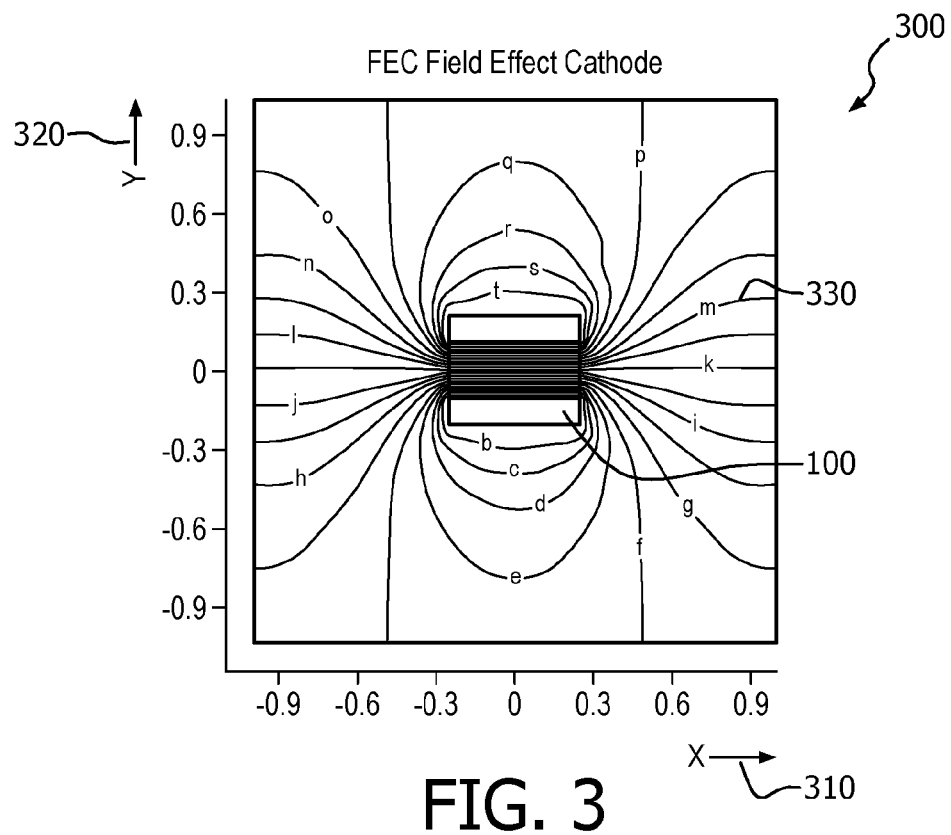
FIG. 3 illustrates electric potential around the radiation-sensitive detector array of FIG. 1, according to the present disclosure.

Referring to FIG. 3, electric potential around the radiation-sensitive detector array of FIG. 1, according to the present disclosure is presented.

The electric potential graph 300 depicts the radiation-sensitive detector array 100 in the middle of the graph, with electric potential lines 330 extending or diverging therefrom. The x-axis 310 represents voltage, whereas the y-axis 320 represents time.

Figure 4:
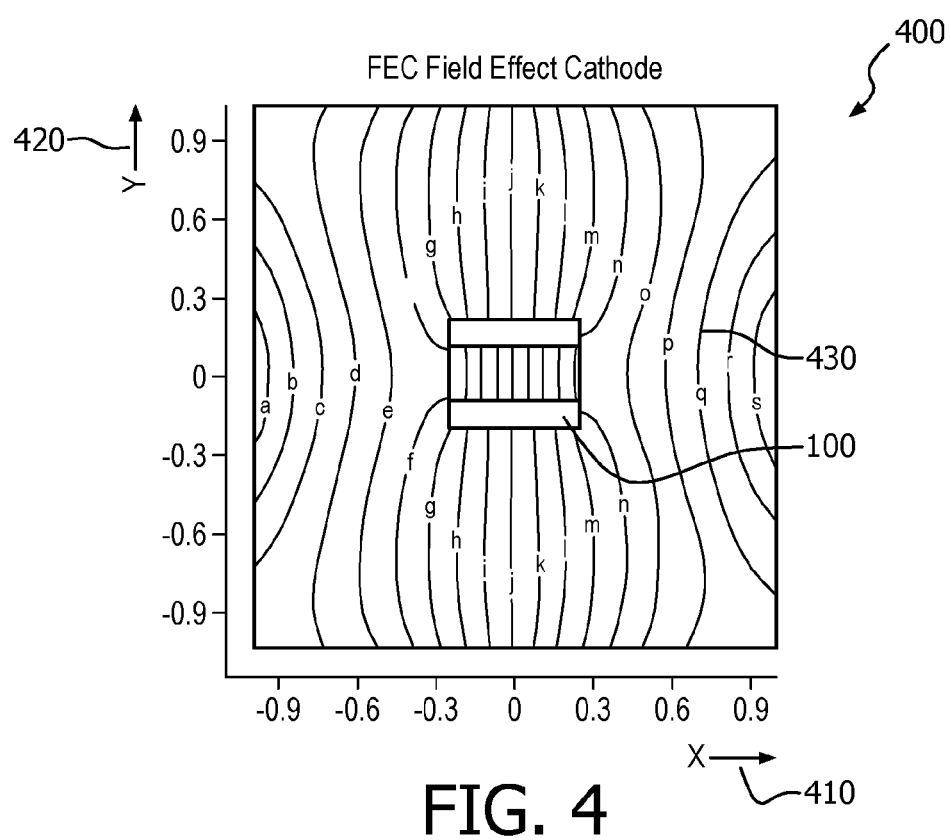
FIG. 4 illustrates intensity of the electric field lines of the radiation-sensitive detector array of FIG. 1, according to the present disclosure.

Referring to FIG. 4, intensity of the electric field lines of the radiation-sensitive detector array of FIG. 1, according to the present disclosure is presented.

The intensity graph 400 depicts the radiation-sensitive detector array 100 in the middle of the graph, with electric field lines 430 extending or diverging therefrom. The x-axis 410 represents voltage, whereas the y-axis 420 represents time.

In FIGS. 3 and 4, the CZT detector substrate 130 may have a thickness of 2 mm and a width of 5 mm. Of course, one skilled in the art may contemplate a plurality of different dimensions for the CZT detector substrate 130.

Figure 5:
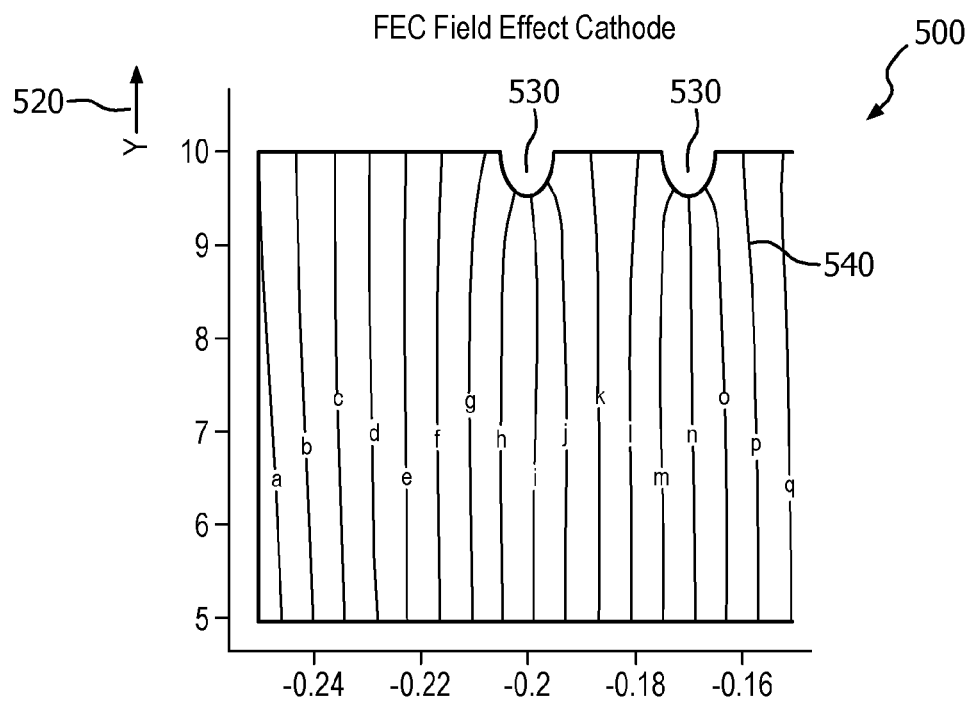
FIG. 5 illustrates electric potential around the non-planar cathode regions, according to the present disclosure.

Referring to FIG. 5, electric potential around the non-planar cathode regions, according to the present disclosure is presented.

The electric potential graph 500 depicts electric potential lines 540 with respect to the non-planar or uneven cathode regions 530. The x-axis 510 represents voltage, whereas the y-axis 520 represents time. The electric potential lines 540 have a tendency of converging onto the non-planar cathode regions 530, where the protrusions 135 of the cathode 120 are located (see FIGS. 1 and 2).

Figure 6:
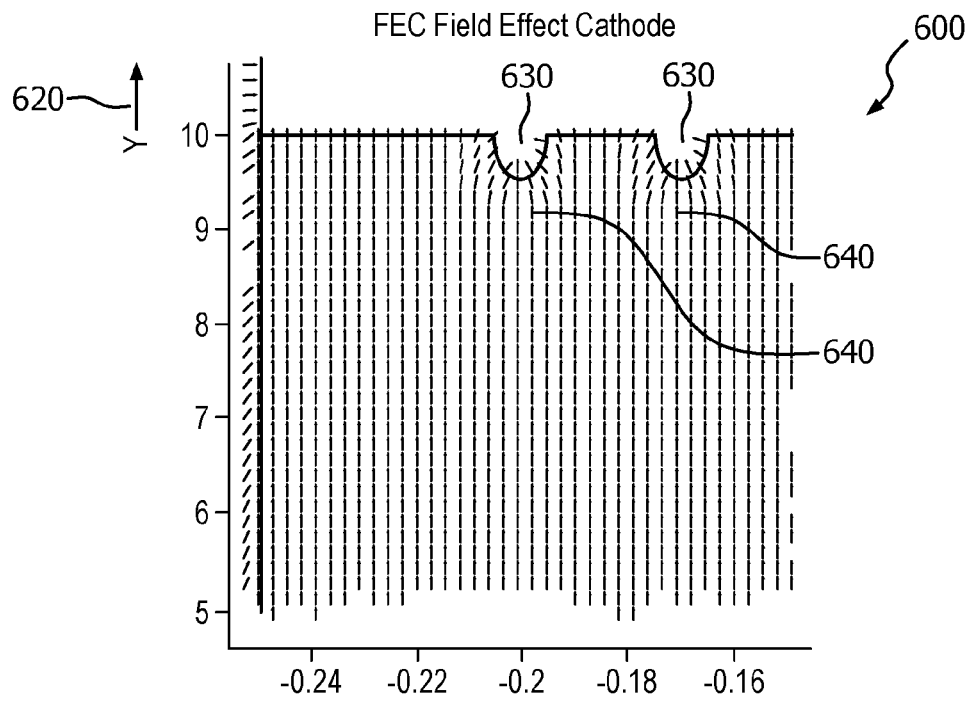
FIG. 6 illustrates electric field lines with arrows pointing toward the non-planar or uneven cathode regions, according to the present disclosure.

Referring to FIG. 6, electric field lines with arrows pointing toward the non-planar cathode regions, according to the present disclosure are presented.

The electric field graph 600 depicts electric field lines 640 with respect to the non-planar or uneven cathode regions 630. The x-axis 610 represents voltage, whereas the y-axis 620 represents time. The electric field lines 640 have a tendency of converging onto the non-planar cathode regions 630, where the protrusions 135 of the cathode 120 are located (see FIGS. 1 and 2).

Figure 7:
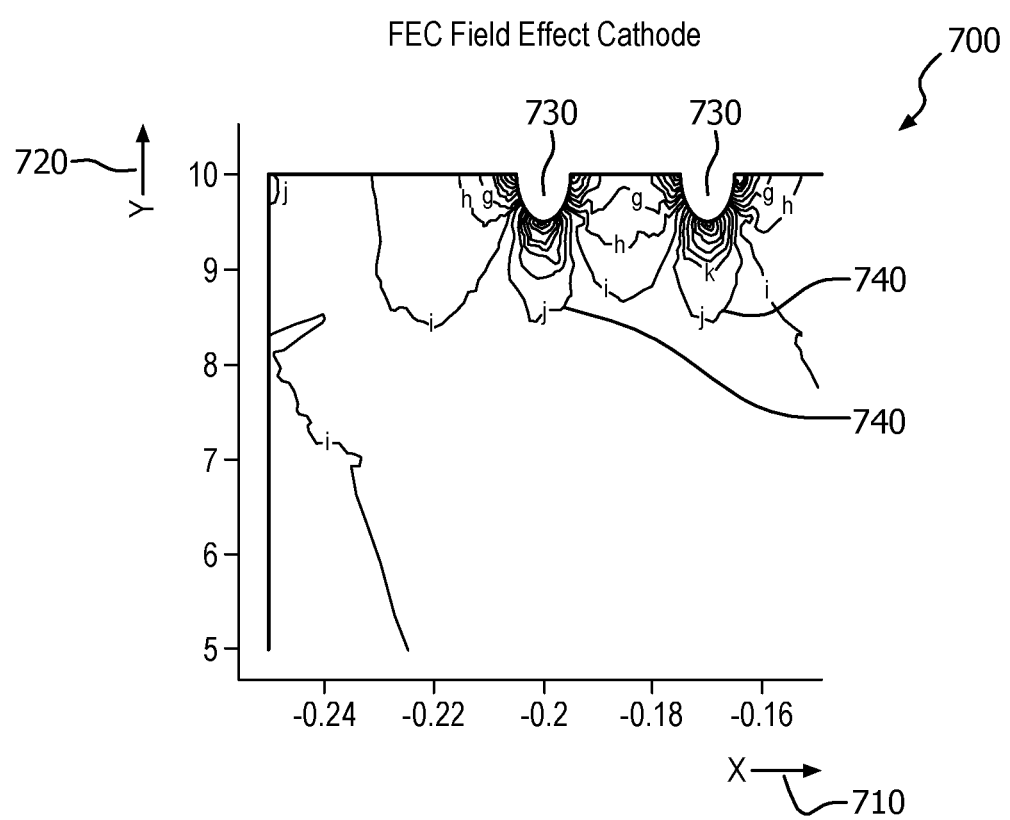
FIG. 7 illustrates electric field intensity around the non-planar or uneven cathode regions, according to the present disclosure.

Referring to FIG. 7, electric field intensity around the non-planar cathode regions, according to the present disclosure is presented.

The field intensity graph 700 depicts intensity lines 740 with respect to the non-planar cathode regions 730. The x-axis 710 represents voltage, whereas the y-axis 720 represents time. The intensity lines 740 have a tendency of converging onto the non-planar cathode regions 730, where the protrusions 135 of the cathode 120 are located (see FIGS. 1 and 2)

In one exemplary embodiment, the detector array 100 is a direct conversion detector array. In another exemplary embodiment, the detector array 100 is a part of a single photon emission computed tomography (CT) scanner, described below.

Figure 8:
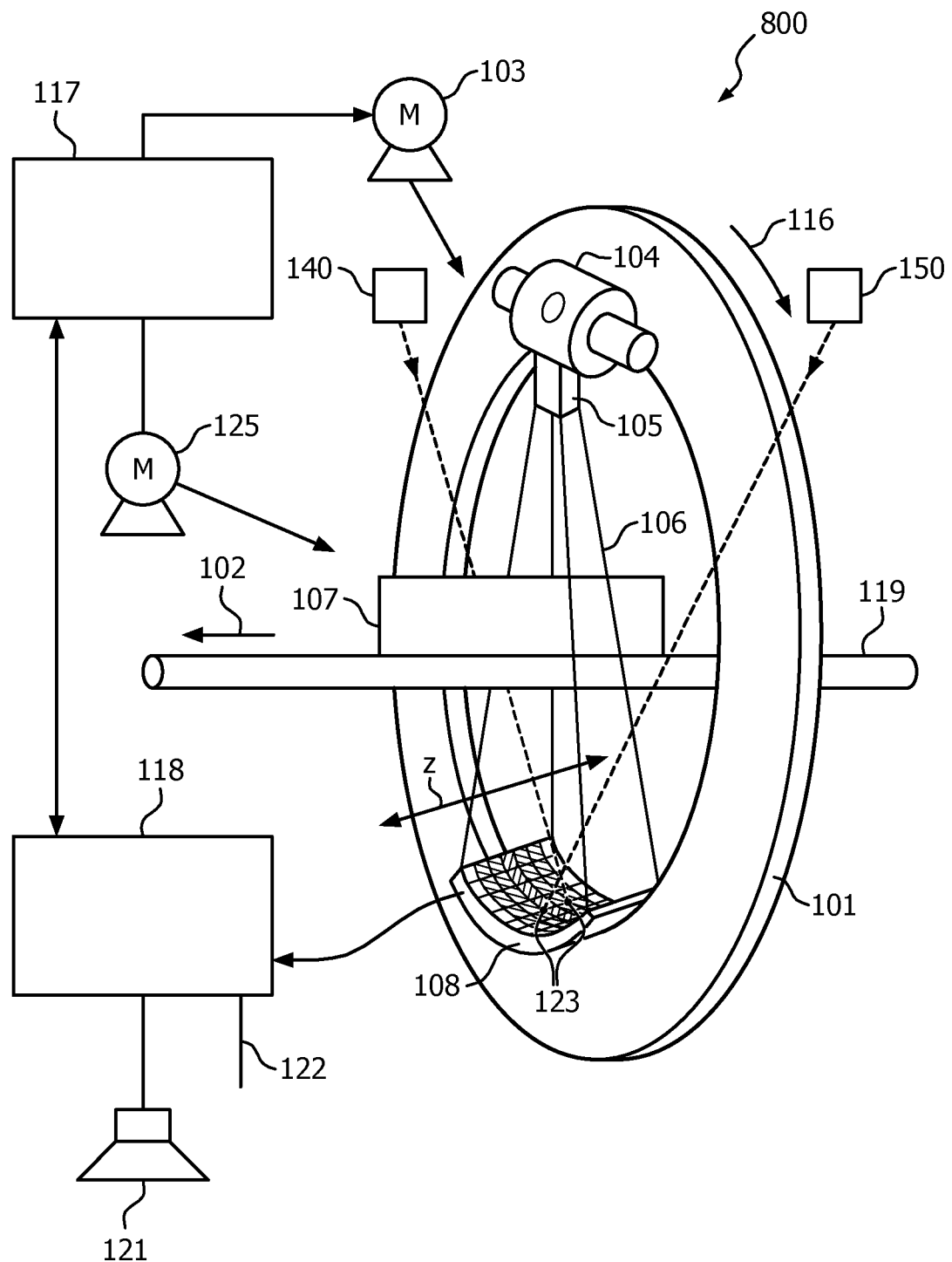
FIG. 8 is a computed tomography (CT) apparatus, according to the present disclosure.

Referring to FIG. 8, there is shown a computed tomography (CT) apparatus, according to the present disclosure.

The computed tomography apparatus 800 depicted in FIG. 1 is a cone-beam CT scanner. However, the present disclosure may also be carried out with a fan-beam geometry. The CT scanner depicted in FIG. 8 comprises a gantry 101 housed within or attached to a stationary gantry (not shown), which is rotatable around a rotational axis 102. The gantry 101 is driven by means of a motor 103. Reference numeral 104 designates a main source of radiation such as an X-ray source, which, according to an aspect of the present disclosure, emits polychromatic or monochromatic radiation.

Reference numeral 105 designates an aperture system, such as a collimator, which forms the radiation beam emitted from the radiation source to a cone-shaped radiation beam 106. The cone-beam 106 is directed such that it penetrates an object of interest 107 arranged in the center of the gantry 101, i.e., in an examination region of the CT scanner, and impinges onto a detector 108. As may be taken from FIG. 8, the detector 108 is arranged on the gantry 101 opposite to the main source of radiation 104, such that the surface of the detector 108 is covered by the cone beam 106. The detector 108 depicted in FIG. 8 comprises a plurality of detector elements 123 each capable of detecting, in an energy-resolving manner or in a non-energy-resolving manner, X-rays which have been scattered by the object of interest 107.

During a scan of the object of interest 107, the source of radiation 104, the aperture system 105 and the detector 108 are rotated along the gantry 101 in the direction indicated by an arrow 116. For rotation of the gantry 101 with the source of radiation 104, the aperture system 105 and the detector 108, the motor 103 is connected to a motor control unit 117, which is connected to a calculation or determination unit 118.

In FIG. 8, the object of interest 107 is an item of baggage which is disposed on a conveyor belt 119. During the scan of the object of interest 107, while the gantry 101 rotates around the item of baggage 107, the conveyor belt 119 may or may not displace the object of interest 107 along a direction parallel to the rotational axis 102 of the gantry 101. By this, the object of interest 107 is scanned along a circular scan path (when the conveyor belt 119 does not displace the object of interest 107) or along a helical scan path (when the conveyor belt 119 does displace the object of interest 107). The conveyor belt 119 may be stationary or may move and may also be stopped during the scans to thereby measure signal slices. Instead of providing a conveyor belt 119, for example in medical applications where the object of interest 107 is a patient, a moveable table, such as a support couch, is used. However, it should be noted that in all of the described cases it is also possible to perform a helical scan, where there is a displacement in a direction parallel to the rotational axis 102, and additionally the rotation of the gantry 101 around the rotational axis 102. Alternatively, in all of the described cases it is also possible to perform a circular scan, where there is no displacement in a direction parallel to the rotational axis 102, but only the rotation of the gantry 101 around the rotational axis 102.

Further, it shall be emphasized that, as an alternative to the cone-beam configuration shown in FIG. 8, the present disclosure can be realized by a fan-beam configuration. In order to generate a primary fan-beam, the aperture system 105 can be configured as a slit collimator.

The detector 108 is connected to the determination unit 118. The determination unit 118 receives the detection result, i.e., the read-outs from the detector elements 123 of the detector 108 and determines a scanning result on the basis of these read-outs. Furthermore, the determination unit 118 communicates with the motor control unit 117 in order to coordinate the movement of the gantry 101 with motors 103 and 120 with the conveyor belt 119.

The determination unit 118 is adapted for reconstructing an image from read-outs of the detector 108. A reconstructed image generated by the calculation unit 118 may be output to a display (not shown in FIG. 8) via an interface 122.

The determination unit 118 may be realized by a data processor to process read-outs from the detector elements 123 of the detector 108. Furthermore, as may be taken from FIG. 8, the determination unit 118 may be connected to a loudspeaker 121, for example to automatically output an alarm in case of the detection of suspicious material in the item of baggage 107.

The CT apparatus 800 for examination of the object of interest 107 includes the detector 108 having the plurality of detecting elements 123 arranged in a matrix-like manner, each being adapted to detect X-rays passing through the object of interest 107. Further, the CT apparatus 800 comprises the determination unit 118 adapted to determine structural information concerning the object of interest 107 based on an analysis of detecting signals received from the detecting elements 123.

The CT apparatus 800 comprises the main X-ray source 104 adapted to emit X-rays to the object of interest 107. The collimator 105 provided between the electromagnetic radiation source 104 and the detecting elements 123 is adapted to collimate an electromagnetic radiation beam emitted from the electromagnetic radiation source 104 to form a cone-beam. Alternatively, not shown in FIG. 8, a slit collimator can be used instead of collimator 105 to produce a fan-beam. The detecting elements 123 form a multi-slice detector array 108. The CT apparatus 800 is configured as a baggage inspection apparatus.

The CT apparatus 800 for examination an object of interest 107 comprises in addition to the main or first electromagnetic radiation source 104 a first auxiliary electromagnetic radiation source 140 and a second auxiliary electromagnetic radiation source 150 both being adapted as X-ray tubes to emit electromagnetic radiation to the object of interest 107. The detector 108 is further adapted to detect electromagnetic radiation generated by the main electromagnetic radiation source 104 or generated by the auxiliary electromagnetic radiation sources 140, 150 and scattered on the object of interest 107. The determination unit 108 is adapted to determine structural information concerning the object of interest 107 based on an analysis of detecting signal received from the detecting device 108.

Thus, the radiation-sensitive detector array 100 of FIG. 1 may be utilized in cooperation with the CT apparatus 800 of FIG. 8 in order to reduce the polarization.

Moreover, in certain exemplary embodiments, the cathode 120 is constructed by milling the CZT detector substrate 130. After milling is completed, a polishing procedure may be performed on the CZT detector substrate 130. The polishing is an optional step. One skilled in the art may contemplate a plurality of different methods for forming or constructing the protrusions 135 across the surface of the cathode 120 and a plurality of milling and polishing methodologies.

Additionally, the current emitted from the cathode 120 may be given by the Richardson Dushman equation. This increase in surface electric field of about E=3000V/cm causes a emission barrier lowering of about $\Delta\Phi = -\beta_S * E^{1/2} = -0.021$ eV for Schottky constant ($\beta_S = 4 \times 10^{-5}$ ev/(V/m)$^{1/2}$). And this barrier lowering causes an increased emission current from the intrusions of $I_{FEC}/I = \exp(\Delta\Phi/kT) = 2$.

Finally, it is pointed out that in the present application the term "comprising" does not exclude other elements or steps, that "a" or "an" does not exclude a plurality, and that a single processor or other unit may fulfill the functions of several means. The present disclosure resides in each and every novel characteristic feature and each and every combination of characteristic features. Moreover, any reference signs in the claims shall not be construed as limiting their scope.

The foregoing examples illustrate various aspects of the present disclosure and practice of the methods of the present disclosure. The examples are not intended to provide an exhaustive description of the many different embodiments of the present disclosure. Thus, although the foregoing present disclosure has been described in some detail by way of illustration and example for purposes of clarity and understanding, those of ordinary skill in the art will realize readily that many changes and modifications may be made thereto without departing form the spirit or scope of the present disclosure. Therefore, the above description should not be construed as limiting, but merely as exemplifications of particular embodiments. Those skilled in the art will envision other modifications within the scope and spirit of the claims appended hereto.

What is claimed is:

1. A radiation-sensitive detector array, comprising:
    a first side;
    a second side in opposed relation to the first side; and
    a detector substrate positioned between the first and second sides;
    wherein the first side is constructed as a series of protrusions with peaks adapted and dimensioned to cause electric field lines to converge thereon.

2. The radiation-sensitive detector array as in claim 1, wherein the protrusions are equally spaced apart and extend towards the second side.

3. The radiation-sensitive detector array of claim 2, wherein each of the protrusions is of a pyramidal construction.

4. The radiation-sensitive detector array of claim 3, wherein each of the peaks of the pyramidal construction protrusions has a tip with a rounded edge.

5. The radiation-sensitive detector array of claim 3, wherein each of the peaks of the pyramidal constructions protrusions has a tip with a sharp edge.

6. The radiation-sensitive detector array of claim 1, wherein the electric field lines are at least ten times stronger at the peaks of each of the pyramidal constructions than at other regions of the detector substrate.

7. The radiation-sensitive detector array as in claim 1, wherein the detector array is a direct conversion detector array.

8. The radiation-sensitive detector array as in claim 1, wherein the detector array is a part of a single photon emission computed tomography (CT) scanner.

9. The radiation-sensitive detector array as in claim 1, wherein the first side is a cathode and the second side is an anode.

10. The radiation-sensitive detector array as in claim 9, wherein the cathode is constructed by milling the detector substrate.

11. The radiation-sensitive detector array of claim 10, wherein a polishing procedure is performed after milling the detector substrate.

12. A radiation-sensitive detector array, comprising:
    a field emission cathode;
    an anode in opposed relation to the field emission cathode; and
    a Cadmium Zinc Telluride detector substrate positioned between the field emission cathode and the anode,
    wherein the field emission cathode is constructed as a non-planar shape.

13. The radiation-sensitive detector array as in claim 1, wherein the first and second sides detect incident radiation, whereas the detector substrate produces a signal indicative of the detected radiation.

14. A method for concentrating electric field lines in a radiation-sensitive detector array, the method comprising:
    constructing a first side as a non-planar shape;
    positioning a first side in opposed relation to the second side;
    milling a detector substrate to form a complementary non-planar shape;
    polishing the detector substrate after completing of milling; and
    positioning the detector substrate between the first and second sides.

15. The method as in claim 14, wherein the non-planar shape of the first side is a series of equally spaced apart protrusions.

16. The method of claim 15, wherein the constructing step comprises forming a pyramidal construction.

17. The method of claim 16, wherein each of the pyramidal constructions includes a peak, the peak adapted and dimensioned to cause electric field lines to converge thereon.

18. The method of claim 15, wherein the constructing step comprises forming a rounded construction.

19. The method as in claim 14, wherein the detector substrate is a Cadmium Zinc Telluride (CZT) detector substrate.

20. The method as in claim 19, further comprising polishing the CZT detector substrate after completion of milling.

* * * * *